(12) United States Patent
Smith et al.

(10) Patent No.: US 9,751,294 B2
(45) Date of Patent: Sep. 5, 2017

(54) SYSTEMS AND METHODS FOR TRANSLATING THREE DIMENSIONAL GRAPHIC MOLECULAR MODELS TO COMPUTER AIDED DESIGN FORMAT

(71) Applicant: PerkinElmer Informatics, Inc., Waltham, MA (US)

(72) Inventors: Robin Y. Smith, Boston, MA (US); Andrew Smellie, Candia, NH (US); Nisarg Mehta, Boston, MA (US)

(73) Assignee: PerkinElmer Informatics, Inc., Waltham, MA (US)

( * ) Notice: Subject to any disclaimer, the term of this patent is extended or adjusted under 35 U.S.C. 154(b) by 654 days.

(21) Appl. No.: 14/274,163

(22) Filed: May 9, 2014

(65) Prior Publication Data

US 2014/0336807 A1   Nov. 13, 2014

Related U.S. Application Data

(60) Provisional application No. 61/821,416, filed on May 9, 2013.

(51) Int. Cl.
| | |
|---|---|
| *B33Y 50/00* | (2015.01) |
| *G06F 17/50* | (2006.01) |
| *G06F 19/00* | (2011.01) |
| *G03F 7/00* | (2006.01) |
| *B29C 67/00* | (2017.01) |

(52) U.S. Cl.
CPC .............. *B33Y 50/00* (2014.12); *G06F 17/50* (2013.01); *G06F 19/708* (2013.01); *B29C 67/0059* (2013.01); *G03F 7/00* (2013.01)

(58) Field of Classification Search
None
See application file for complete search history.

(56) References Cited

U.S. PATENT DOCUMENTS

| | | | |
|---|---|---|---|
| 4,967,372 | A | 10/1990 | Feldman |
| 5,249,137 | A | 9/1993 | Wilson et al. |
| 5,386,507 | A | 1/1995 | Teig et al. |
| 5,434,971 | A | 7/1995 | Lysakowski, Jr. |
| 5,461,580 | A | 10/1995 | Facci et al. |
| 5,555,366 | A | 9/1996 | Teig et al. |

(Continued)

FOREIGN PATENT DOCUMENTS

| | | |
|---|---|---|
| EP | 1526471 A1 | 4/2005 |
| GB | 2493830 A | 2/2013 |

(Continued)

OTHER PUBLICATIONS

Jenny, "3D-Printed Enzyme—Proof of Concept", Oct. 31, 2012.*

(Continued)

*Primary Examiner* — Qing Wu
(74) *Attorney, Agent, or Firm* — Choate, Hall & Stewart, LLP; William R. Haulbrook

(57) ABSTRACT

Described herein are systems, methods, and apparatus that allow a user to convert various styles of three dimensional graphic representations of molecular models to computer aided design format to enable printing of a physical model using three dimensional printing equipment such as rapid prototyping equipment, additive manufacturing equipment, and/or three dimensional printers.

22 Claims, 7 Drawing Sheets

(56) References Cited

U.S. PATENT DOCUMENTS

| | | |
|---|---|---|
| 6,017,390 A | 1/2000 | Charych et al. |
| 6,304,869 B1 | 10/2001 | Moore et al. |
| 6,434,490 B1 | 8/2002 | Agrafiotis et al. |
| 7,043,415 B1 | 5/2006 | Dunlavey et al. |
| 7,250,950 B2 | 7/2007 | Smith et al. |
| 7,613,574 B2 | 11/2009 | Verseput |
| 7,650,327 B2 | 1/2010 | Remsen et al. |
| 7,663,607 B2 | 2/2010 | Hotelling et al. |
| 7,676,499 B2 | 3/2010 | Dorsett, Jr. |
| 7,705,830 B2 | 4/2010 | Westerman et al. |
| 7,707,206 B2 | 4/2010 | Encina et al. |
| 7,805,437 B1 | 9/2010 | Andersson et al. |
| 7,912,689 B1 | 3/2011 | Helson |
| 8,407,578 B2 | 3/2013 | Boyer et al. |
| 8,433,723 B2 | 4/2013 | Smith et al. |
| 8,538,983 B2 | 9/2013 | Huang et al. |
| 8,854,361 B1 | 10/2014 | Smith |
| 9,031,977 B2 | 5/2015 | Smith et al. |
| 9,430,127 B2 | 8/2016 | Smith et al. |
| 9,535,583 B2 | 1/2017 | Smellie et al. |
| 2002/0049548 A1 | 4/2002 | Bunin |
| 2002/0051999 A1 | 5/2002 | Sepetov et al. |
| 2002/0107359 A1 | 8/2002 | Hogarth et al. |
| 2002/0161599 A1 | 10/2002 | Faerman et al. |
| 2003/0194687 A1 | 10/2003 | Clark |
| 2004/0003000 A1 | 1/2004 | Smith et al. |
| 2004/0006742 A1 | 1/2004 | Slocombe |
| 2004/0024493 A1 | 2/2004 | Fagrell et al. |
| 2004/0088118 A1 | 5/2004 | Jensen et al. |
| 2004/0122641 A1 | 6/2004 | Miller et al. |
| 2004/0171062 A1 | 9/2004 | Hirth et al. |
| 2004/0236740 A1 | 11/2004 | Cho et al. |
| 2004/0249791 A1 | 12/2004 | Waters et al. |
| 2005/0010603 A1 | 1/2005 | Berks |
| 2005/0094205 A1 | 5/2005 | Lo et al. |
| 2005/0102313 A1 | 5/2005 | Levering et al. |
| 2005/0123993 A1 | 6/2005 | Brunner et al. |
| 2005/0131894 A1 | 6/2005 | Vuong |
| 2005/0177280 A1 | 8/2005 | Almstetter et al. |
| 2005/0226495 A1 | 10/2005 | Li |
| 2006/0040322 A1 | 2/2006 | Archetti et al. |
| 2006/0061595 A1 | 3/2006 | Goede et al. |
| 2006/0123113 A1 | 6/2006 | Friedman |
| 2006/0277201 A1 | 12/2006 | Dorsett |
| 2007/0016853 A1 | 1/2007 | Abagyan et al. |
| 2007/0174765 A1 | 7/2007 | Schleppenbach et al. |
| 2007/0177803 A1 | 8/2007 | Elias et al. |
| 2007/0192747 A1 | 8/2007 | Phelan et al. |
| 2007/0260583 A1 | 11/2007 | Domine et al. |
| 2007/0276636 A1 | 11/2007 | Wythoff |
| 2008/0004810 A1 | 1/2008 | Boyer et al. |
| 2008/0036743 A1 | 2/2008 | Westerman et al. |
| 2008/0136785 A1 | 6/2008 | Baudisch et al. |
| 2008/0140616 A1 | 6/2008 | Encina et al. |
| 2008/0165140 A1 | 7/2008 | Christie et al. |
| 2008/0213663 A1 | 9/2008 | Hu et al. |
| 2008/0228774 A1 | 9/2008 | Hamilton et al. |
| 2008/0234135 A1 | 9/2008 | Ghosh et al. |
| 2008/0234996 A1 | 9/2008 | Ghosh et al. |
| 2008/0309632 A1 | 12/2008 | Westerman et al. |
| 2009/0006411 A1 | 1/2009 | Lele et al. |
| 2009/0063427 A1 | 3/2009 | Zuta et al. |
| 2009/0171975 A1 | 7/2009 | McConnell et al. |
| 2009/0273571 A1 | 11/2009 | Bowens |
| 2010/0257457 A1 | 10/2010 | De Goes |
| 2011/0072339 A1 | 3/2011 | Boyer et al. |
| 2011/0163944 A1 | 7/2011 | Bilbrey et al. |
| 2011/0221656 A1 | 9/2011 | Haddick et al. |
| 2011/0276589 A1 | 11/2011 | Smith et al. |
| 2012/0019488 A1 | 1/2012 | McCarthy |
| 2012/0078853 A1 | 3/2012 | Huang et al. |
| 2012/0109972 A1 | 5/2012 | Boyer et al. |
| 2012/0110486 A1 | 5/2012 | Sirpal et al. |
| 2012/0154440 A1 | 6/2012 | Nicholls et al. |
| 2012/0173622 A1 | 7/2012 | Toledano et al. |
| 2012/0185513 A1 | 7/2012 | Samukawa |
| 2012/0188147 A1 | 7/2012 | Hosein et al. |
| 2012/0246228 A1 | 9/2012 | Udezue et al. |
| 2012/0284638 A1 | 11/2012 | Cutler et al. |
| 2012/0311038 A1 | 12/2012 | Trinh et al. |
| 2012/0324368 A1 | 12/2012 | Putz et al. |
| 2013/0044042 A1 | 2/2013 | Olsson et al. |
| 2013/0061163 A1 | 3/2013 | Clark et al. |
| 2013/0218878 A1 | 8/2013 | Smith et al. |
| 2013/0222265 A1 | 8/2013 | Smith et al. |
| 2013/0297058 A1* | 11/2013 | Griffith .................. G06F 17/50 700/98 |
| 2014/0042670 A1* | 2/2014 | Pettis .................. B29C 67/0088 264/401 |
| 2014/0082015 A1 | 3/2014 | Huang et al. |
| 2014/0089329 A1 | 3/2014 | Kozloski et al. |
| 2014/0173475 A1 | 6/2014 | Smellie et al. |
| 2014/0173476 A1 | 6/2014 | Smellie et al. |
| 2014/0267240 A1 | 9/2014 | Smith |
| 2014/0282106 A1 | 9/2014 | Smith et al. |
| 2014/0301608 A1 | 10/2014 | Karthikeyan |
| 2014/0337725 A1 | 11/2014 | Smith et al. |
| 2015/0051889 A1 | 2/2015 | Ohrn et al. |
| 2015/0112604 A1 | 4/2015 | Smith |
| 2015/0199797 A1 | 7/2015 | Palo |

FOREIGN PATENT DOCUMENTS

| | | |
|---|---|---|
| WO | WO-2007092842 A2 | 8/2007 |
| WO | WO-2011140148 A1 | 11/2011 |
| WO | WO-2013/126077 A1 | 8/2013 |

OTHER PUBLICATIONS

"Phlegmatic prototyping", Apr. 2, 2012.*
Waterman, "Preparing 3D Models" Apr. 1, 2012.*
Kawakami, "A soft and transparent handleable protein model", Aug. 8, 2012, American Institute of Physics.*
"Introduction to Drawing (iPhone)", http://molmatinf.com/introdrawios.html, Molecular Materials Informatics, Inc., Dec. 9, 2010, retrieved by Archive.org as https://web.archive.org/web/20120413131358/http:l/molmatinf.com/introdrawios.html on Apr. 13, 2012.
"Overview of Drawing Gestures (iPhone)", http://molmatinf.com/gesturesios.html, Molecular Materials Informatics, Inc., Nov. 3, 2010, retrieved by Archive.org as https://web.archive.org/web/20101118005114/http:l/molmatinf.com/gesturesios.html on Nov. 18, 2010.
Cambridgesoft, Inc., Chem & Bio Draw, Version 12.0, 24 pages, 2009.
Cambridgesoft, Inc., ChemDraw User's Guide, Version 9.0.1, 23 pages, 2004.
ChemJuice Grande-Basic Structure Drawing, printout page of YouTube video posting from IOBS at http://www.youtube.com/watch?v=mKOcC5bLzdO, <http://www.youtube.com/watch?v=mKOcC5bLzdO>uploaded Oct. 3, 2011, printed May 18, 2015, 2 pages.
IDBS Makes Chemical Structure Drawing Mobile, Press Release, ID Business Solutions, Ltd., 2 pages, Dec. 9, 2009.
Logtenberg, Jeroen, Multi-user interaction with molecular visualizations on a multi-touch table, MSc thesis, Human Media Interaction Group, University of Twente, 48 pages, Aug. 11, 2009.
Mills, Nancy, ChemDraw Ultra 10.0, Journal of American Chemical Society, 128(41):13649-13650, 2006.
Mobile Molecular DataSheet, http://molmatinf.com/mmdsios.html, <http://molmatinf.com/mmdsios.html>Molecular Materials Informatics, Inc., Sep. 23, 2011, retrieved by Archive.org as https://web.archive.org/web/20120403140454/http:l/molmatinf.com/mmdsios.html on Apr. 3, 2012, 4 pages.
MoiPrime+, http://molmatinf.com/molprimeplus.html, <http://molmatinf.com/molprimeplus.html>Molecular Materials Informatics, Inc., Jan. 23, 2011, 13 pages.
Algorri et al., Reconstruction of Chemical Molecules from Images, 2007 Annual International Conference of the IEEE Engineering in

(56) References Cited

OTHER PUBLICATIONS

Medicine and Biology Society (EMBC '07), Lyon, France, Aug. 22-26, 2007, in Conjunction with the Biennial Conference of the Societe Francaise de Genie Biologique et Medical (SFGB), Aug. 22, 2007, pp. 4609-4612.
Australian Patent Application No. 2011248243, APO Examination Report No. 1, issued Nov. 5, 2013, 3 pages.
Bennett, Samsung's AllShare Play pushes pictures from phone to cloud and TV, <http://news.cnet.com/8301-1035_3-57391735-94/samsungs-allshare-play-pushes-pictures-from-phone-to-cloud-and-tv/> [retrieved Oct. 24, 2013], Mar. 6, 2012, 9 pages.
Carmigniani, J. et al., Augmented Reality Technologies, Systems and Applications, Multimedia Tools and Applications 51:341-377, (2011).
Casey et al., Optical Recognition of Chemical Graphics, Document Analysis and Recognition, 1993, Proceedings of the Second International Conference on, Tsukuba Science City, Japan, Oct. 20-22, 1993, Los Alamitos, CA, USA, IEEE Comput. Soc., Oct. 20, 1993, pp. 627-631.
Chinese First Office Action, Application No. 201190000597.X, mailed May 29, 2013, 4 pages Including Translation.
Clark A. M., Basic Primitives for Molecular Diagram Sketching, Journal of Cheminformatics 2:8 (2010).
European Search Report for 13275308.8, Aug. 13, 2014, 8 pages.
European Search Report for 13275308.8, Apr. 9, 2014, 5 pages.
Filippov et al., Optical Structure Recognition Software to Recover Chemical Information: OSRA, An Open Source Solution, Journal of Chemical Information and Modeling, vol. 49, No. 3, Mar. 23, 2009, pp. 740-743.
Flick—Simply the easiest way to share, <http://getflick.io/> [retrieved Aug. 23, 2013], 4 pages.
Furlon, Rod, Build Your Own Google Glass, Resources Hands On, IEEE Spectrum, IEEE Inc., vol. 50, No. 1, pp. 20-21, (Jan. 1, 2013).
Giudice N. A. et al., Learning Non-Visual Graphical Information Using a Touch-Based Vibro-Audio Interface, Proceedings of the 14th International ACM Sigaccess Conference on Computers and Accessibility, Assets '12, 103-110 (Jan. 1, 2012).
Gonzalez-Villanueva et al., WallShare: A Collaborative Multi-pointer System for Portable Devices, Nov. 19, 2012, 7 pages.
International Search Report for PCT/US2011/035070, Oct. 6, 2011, 4 pages.
International Search Report for PCT/US2012/026574, Mar. 20, 2013, 4 pages.
International Search Report for PCT/US2014/016249, Aug. 13, 2014, 4 pages.
International Search Report for PCT/US2014/035685, Aug. 4, 2014, 4 pages.
iTunes Preview, Flick for iPhone, iPad, and iPod touch on the iTunes App Store, <https://itunes.apple.com/us/app/flick./id644265534?mt=8> [retrieved Oct. 28, 2013], 2 pages.
Jurach, T., Microsoft Outlook Quick Start Email Guide!, 1-3 (2006).
Kim et al., Development of a Gesture-Based Molecular Visualization Tool Based on Virtual Reality for Molecular Docking, Bull. Korean Chem. Soc. 2004, vol. 25, No. 10 pgs, 1571-1574.
Layar, What is Layar?, <http://www.layar.com/features/> [retrieved Nov. 14, 2012], 7 pages.
Li et al., Personal Experience with Four Kinds of Chemical Structure Drawing Software: Review on ChemDraw, ChemWindow, ISIS/Draw, and ChemSketch, J. Chem. Inf. Comput. Sci. 44:1886-1890 (2004).
Lorensen et al., Marching Cubes: A high resolution 3D surface construction algorithm. In: Computer Graphics, vol. 21, No. 4, Jul. 1987.
Lucero et al., Pass-Them-Around: Collaborative Use of Mobile Phones for Photo Sharing, CHI 2011—Session: Photo Sharing, May 7-11, 2011, Vancouver, BC, Canada, 10 pages.
Park et al., Automated Extraction of Chemical Structure Information From Digital Raster Images, Chemistry Central Journal, Biomed Central Ltd., vol. 3, No. 1, Feb. 5, 2009, pp. 1-16.
Park et al., Tunable Machine Vision-Based Strategy for Automated Annotation of Chemical Databases, Journal of Chemical Information and Modeling, vol. 49, No. 8, 2009, pp. 1993-2001.
Pering et al., Enabling Pervasive Collaboration with Platform Composition, Intel Research Santa Clara, 2009, 18 pages.
Pering et al., Spontaneous Marriages of Mobile Devices and Interactive Spaces, Communications of the ACM, Sep. 2005, vol. 48, No. 9, pp. 53-59, 7 pages.
Scheible et al., MobiToss: A Novel gesture based interface for creating and sharing mobile multimedia art on large public displays, MM'08, Oct. 26-31, 2008 Vancouver British Columbia, Canada, pp. 957-960, 4 pages.
Shine et al., ChemPad3 a tutorial, May 21, 2008, 10 pages.
Toennies J. L. et al., Toward Haptic/Aural Touchscreen Display of Graphical Mathematics for the Education of Blind Students, WHC, IEEE, 373:378 (2011).
Tsotsis, Word Lens Translates Words Inside of Images. Yes Really., <http://techcrunch.com/2010/12/16/world-lens-translates-words-inside-of-images-yes-really/> [retrieved Nov. 14, 2012], Dec. 16, 2010, 3 pages.
Valko et al., CLiDE Pro: The Latest Generation of CLiDE, a Tool for Optical Chemical Structure Recognition, Journal of Chemical Information and Modeling, vol. 94, No. 4, Apr. 27, 2009, pp. 780-787.
Weinberg et al., ZooZBeat: a Gesture-based Mobile Music Studio, NIME 2009, pp. 312-315, 4 pages.
Williams et al., Mobile apps for chemistry in the world of drug discovery, Drug Discovery Today, vol. 16. Nos. 21/22, Nov. 2011, pp. 928-939.
Williams et al., Smart Phones, a Powerful Tool in the Chemistry Classroom, Journal of Chemical Education, 2011, pp. 683-686.
Wobbrock et al., User-Defined Gestures for Surface Computing, CHI—Tabletop Gestures, Apr. 7, 2009, pp. 1083-1092.
Written Opinion for PCT/US2011/035070, Oct. 6, 2011, 9 pages.
Written Opinion for PCT/US2012/026574, Mar. 20, 2013, 8 pages.
Written Opinion for PCT/US2014/016249, Aug. 13, 2014, 7 pages.
Written Opinion for PCT/US2014/035685, Aug. 4, 2014, 8 pages.
Chemistry World, Mobile chemistry—chemistry in your hands and face, 21 pages (2010), retrieved on Feb. 23, 2017 ,www.chemistryworld.com/opinion/comment/1014923.article>, paragraphs [0019] and [0020] and fig. 1.

* cited by examiner

SYSTEMS AND METHODS FOR TRANSLATING THREE DIMENSIONAL GRAPHIC MOLECULAR MODELS TO COMPUTER AIDED DESIGN FORMAT

RELATED APPLICATIONS

This application claims priority to and the benefit of U.S. Provisional Patent Application No. 61/821,416, titled "Systems and Methods for Translating Three-Dimensional Graphic Molecular Models to Computer Aided Design Format," filed on May 9, 2013, the content of which is hereby incorporated by reference herein, in its entirety.

BACKGROUND

Three dimensional molecular modeling software applications provide users such as chemists, pharmaceutical scientists, molecular biologists, students, and instructors with tools for viewing and manipulating three dimensional graphic representations of chemical structures. Various different types of representations of a particular chemical structure may be available for use, depending upon the individual software package. Common representations of three dimensional graphic molecular models include a ball-and-stick representation, a wire frame representation, and a space filling representation, for example. Software applications used for creating, editing, and/or viewing three dimensional molecular models include Electronic Lab Notebooks (ELN) such as E-Notebook by PerkinElmer of Waltham, Mass.; and chemistry modeling programs such as Chem3D or ChemBio3D by PerkinElmer of Waltham, Mass., and Maestro by Schrodinger of New York, N.Y. Depending upon the software application used, the file format of a three dimensional graphic molecular model may vary. For example, Chem3D and ChemBio3D use a .c3xml file format, while Maestro uses a .mae or Protein Data Bank (PDB) file format. These file formats, unlike standard image files, binary files, or computer aided design files, contain information and data fields specific to representations of molecular models.

The surface of a three dimensional (e.g., polyhedral) object may be represented in a computer aided design environment as a polygon mesh made of a collection of polygon faces of a same size and shape (e.g., triangles, quadrilaterals, etc.) that "wrap" the surface of the object. In mesh generation, adaptive meshes may be employed such that a coarse mesh is provided where there are no fine details upon the surface, and a fine mesh occurs in regions containing detailed features. Adaptive meshes, for example, save in computational requirements and disk storage requirements.

Using computer aided design data, for example, provided in STereoLithography (STL) file format developed by 3D Systems of Rock Hill, S.C. or RP format developed by the OpenRP initiative of Goa, India, a rapid prototyping machine or three dimensional printer may be used to fabricate a physical representation of a three dimensional model.

There is a need for automatic conversion of a three dimensional molecular model to standard computer aided design format to allow for immediate and user-friendly printing of a physical representation of the three dimensional molecular model.

SUMMARY OF THE INVENTION

Described herein are various embodiments of systems, methods, and apparatus that allow a user to convert various styles of three dimensional graphic representations of molecular models to computer aided design format to enable printing of a physical model using three dimensional printing equipment such as rapid prototyping equipment, additive manufacturing equipment, and/or three dimensional printers.

In one aspect, the present disclosure relates to a system for converting graphic representations of three dimensional molecular models into computer-aided design format, the system including a processor and a memory having a set of instructions stored thereon, where the instructions, when executed, cause the processor to receive, within a chemical structure rendering application, a request identifying a three dimensional model (e.g., of a chemical and/or biological structure), where the request is one of a file save request and a print request. The instructions, when executed, may cause the processor to associate the request with conversion to a computer-aided design format, access the three dimensional model, identify a surface region of a graphic representation of the three dimensional model, and convert the surface region into a polygon mesh representation.

In some embodiments, the instructions cause the processor to, after converting the surface region into the polygon mesh representation, identify one or more vertices interior to the surface region of the three dimensional model, and remove the one or more vertices interior to the surface region. In some embodiments, the instructions may cause the processor to, after converting the surface region into the polygon mesh representation, verify the polygon mesh representation includes a continuous surface region. In some embodiments, the instructions may cause the processor to adjust the polygon mesh representation to close one or more openings.

In some embodiments, the instructions cause the processor to identify one or more unprintable features of the graphic representation. In some embodiments, the instructions may cause the processor to identify a type of three dimensional printing equipment, where identifying the one or more unprintable features includes identifying, based upon printer capabilities associated with the type of the three dimensional printing equipment, at least one of the one or more unprintable features. In some embodiments, the instructions may cause the processor to, after identifying the one or more unprintable features, cause presentation of a prompt within a user interface of the application, prompting modification of one or more feature settings of the three dimensional model to convert the graphic representation to a printable graphic representation having printable features. In some embodiments, the instructions may cause the processor to receive an acknowledgement of authorization, and automatically adjust the one or more feature settings.

In some embodiments, the instructions cause the processor to verify the graphic representation includes a self-supporting structure. In some embodiments, the polygon mesh representation may include a triangular mesh. In some embodiments, the instructions may cause the processor to, after converting the surface region into the polygon mesh representation, save the polygon mesh representation as a computer aided design file. In some embodiments, the computer aided design file may be in STL file format.

In some embodiments, the instructions cause the processor to, after converting the surface region into the polygon mesh representation, issue print instructions including the polygon mesh representation to a three dimensional printing equipment. In some embodiments, the three dimensional printing equipment may be one of rapid prototyping equipment, additive manufacturing equipment, and a three dimensional printer.

In some embodiments, the three dimensional model may be one of a ribbon protein model, a space filling model, a cartoon model, and a ball and stick model. In some embodiments, the chemical structure rendering application may be one of an electronic notebook application and a chemistry modeling application. In some embodiments, the three dimensional model may include one or more of an XML file and a PDB file. In some embodiments, the three dimensional model may include a .c3xml file.

In another aspect, the present disclosure describes a method including receiving, by a processor of a computing device, within a chemical structure rendering application, a request identifying a three dimensional model (e.g., of a chemical and/or biological structure), where the request is one of a file save request and a print request. The method may include associating, by the processor, the request with conversion to a computer-aided design format, accessing, by the processor, the three dimensional model, identifying, by the processor, a surface region of a graphic representation of the three dimensional model, and converting, by the processor, the surface region into a polygon mesh representation.

In some embodiments, the method includes printing, by a three dimensional printer, the three dimensional model using the polygon mesh representation.

In another aspect, the present disclosure relates to a non-transitory computer readable medium having instructions stored thereon, where the instructions, when executed by a processor, cause the processor to receive, within a chemical structure rendering application, a request identifying a three dimensional model (e.g., of a chemical and/or biological structure), where the request is one of a file save request and a print request. The instructions, when executed, may cause the processor to associate the request with conversion to a computer-aided design format, access the three dimensional model, identify a surface region of a graphic representation of the three dimensional model, and convert the surface region into a polygon mesh representation.

In some embodiments, the instructions, when executed, cause the processor to print, by a three dimensional printer, the three dimensional model using the polygon mesh representation.

Elements of embodiments described with respect to a given aspect of the invention may be used in various embodiments of another aspect of the invention. For example, it is contemplated that features of dependent claims depending from one independent claim (e.g., an independent system claim) can be used with the subject matter of any of the other independent claims (e.g., an independent method claim or an independent computer readable medium claim).

BRIEF DESCRIPTION OF THE DRAWINGS

The foregoing and other objects, aspects, features, and advantages of the invention will become more apparent and may be better understood by referring to the following description taken in conjunction with the accompanying drawings, in which.

Figure 1:
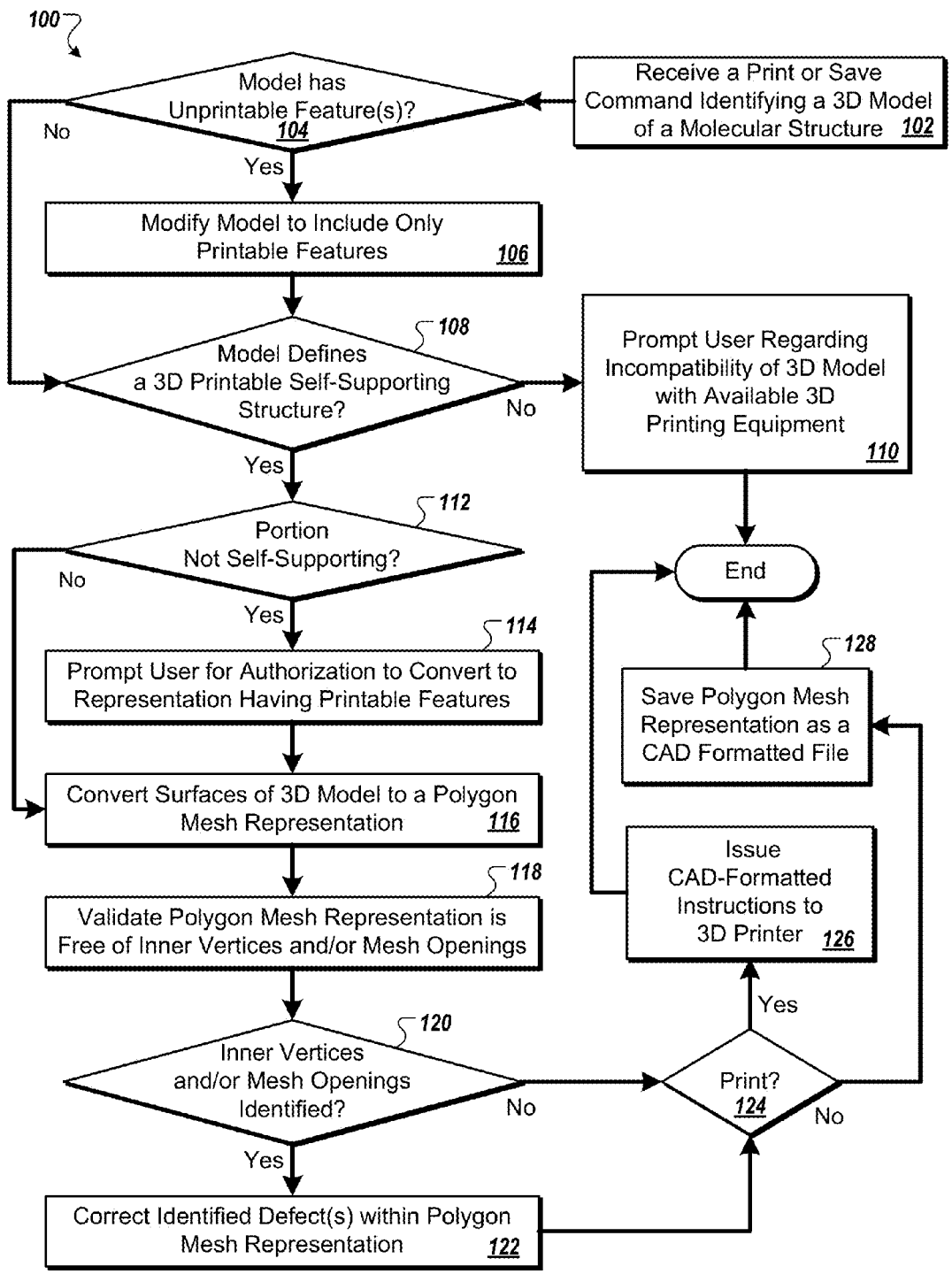
FIG. 1 is a flow chart of an example method for converting a three dimensional graphic representation of a molecular structure to computer aided design format.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

It is contemplated that apparatus, systems, and methods of the claimed invention encompass variations and adaptations developed using information from the embodiments described herein. Adaptation and/or modification of the apparatus, systems, and methods described herein may be performed by those of ordinary skill in the relevant art.

Throughout the description, where apparatus and systems are described as having, including, or comprising specific components, or where processes and methods are described as having, including, or comprising specific steps, it is contemplated that, additionally, there are apparatus and systems of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

In general, in various embodiments, the present disclosure pertains to apparatus, systems, and methods for rendering three dimensional graphic representations of molecular models on a computing device. The computing device may be, for example, a personal computer, a workstation, a tablet computer (e.g., an Apple® IPad® by Apple Inc. of Cupertino, Calif.), or a mobile phone device.

FIG. 1 is a flow chart of an example method 100 for converting a three dimensional graphic representation of a molecular structure to computer aided design format. The method 100, for example, may be performed within an electronic notebook application or chemistry modeling application to convert a three dimensional model to a three dimensional printer ready format such as an STL file.

Figure 2B:
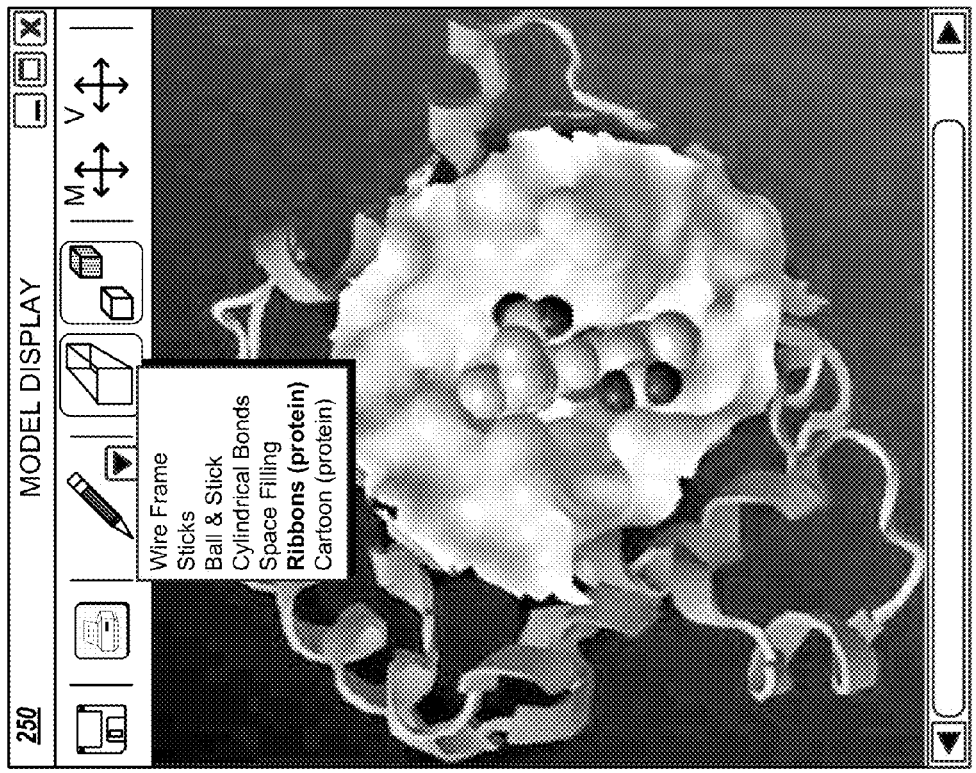
FIGS. 2A and 2B are screen shots depicting additional styles of three dimensional graphic representations of molecular structures eligible for conversion to computer aided design format.
Figure 2A:
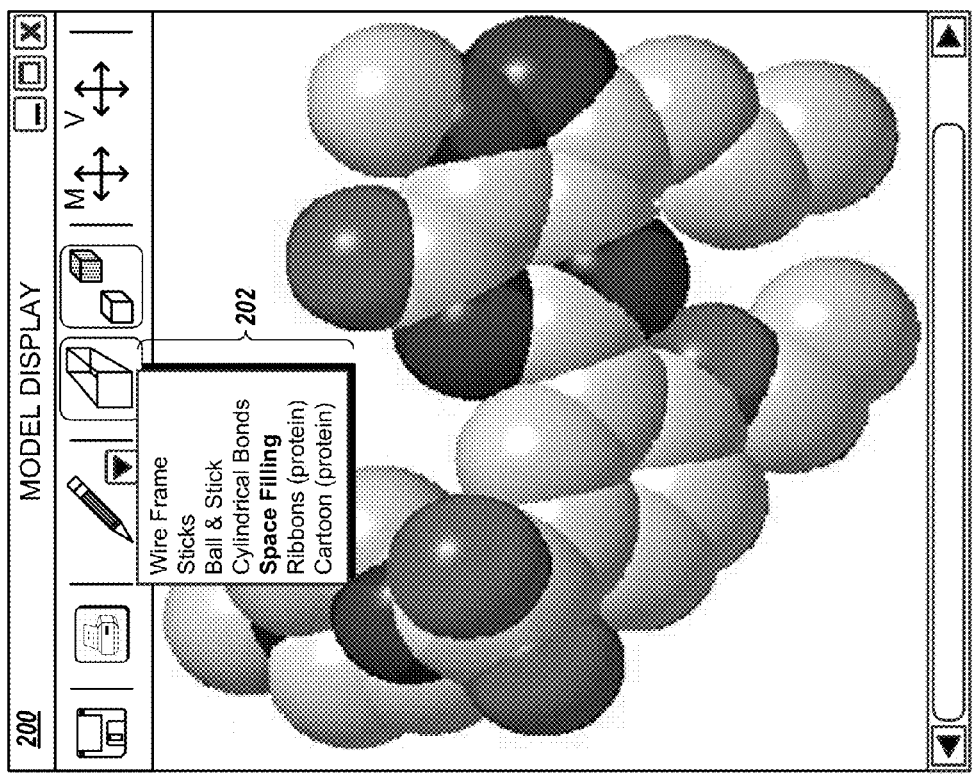
Figure 3A:
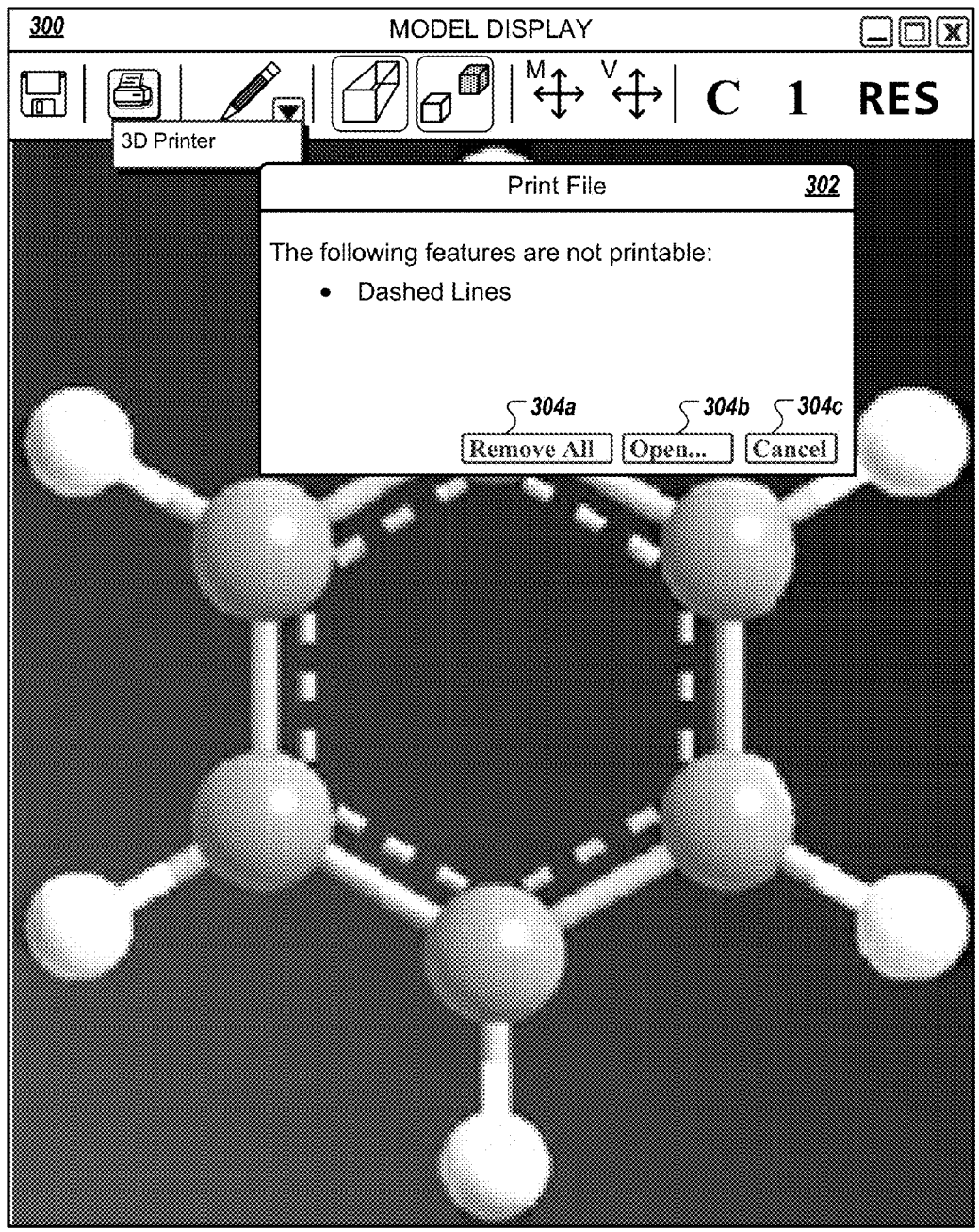
FIGS. 3A through 3C illustrate a series of screen shots depicting conversion of a three dimensional graphic representation of a molecular structure to computer aided design format.

In some implementations, the method 100 begins with receiving a print or save command identifying a three dimensional model of a molecular structure (102). A user may issue a print command designating three dimensional printing equipment such as, in some examples, rapid prototyping equipment, additive manufacturing equipment, or a three dimensional printer. In another example, the user may issue a save command designating a computer aided design file format such as an STL file or an RP file. For example, turning to FIG. 3C, a "save as" dialogue box 342 provides the user with the option of saving an identified model as an STL file. Returning to FIG. 1, the three dimensional model of the molecular structure, in some examples, may be a ribbon protein model (e.g., as illustrated in a screen shot 250 of FIG. 2B), a space filling model (e.g., as illustrated in a screen shot 200 of FIG. 2A), a cartoon model, or a ball and stick model (e.g., as illustrated in a screen shot 300 of FIG. 3A). In some implementations, a single model includes various graphic representations (e.g., space filling, cartoon, ball and stick, etc.). In this circumstance, the command may identify a particular graphic representation. Additionally, a particular graphic representation of a molecular structure may include various visual rendering settings such as, in some examples, visual representation of element symbols, serial numbers, lone pairs, van der Waal radius, and/or delocalized and aromatic bonds. In some implementations, color settings may be on a per-model, per-element, or per-atom setting. For example, individual atom colors may be based upon atom properties (e.g., charge, type, etc.). The three dimensional model, in some implementations, includes an XML file format or PDB file format. The three dimensional model may be stored in a proprietary file format, such as the .c3xml file format by PerkinElmer of Waltham, Mass. or the .mae file format by Schrodinger of New York, N.Y.

In some implementations, the three dimensional model (or graphic representation thereof) is reviewed for one or more unprintable features (104). For example, a wire frame overlay identifying a van der Waal force radius, element symbol markings, and/or serial numbers may be considered unprintable features. In some implementations, unprintable features may be identified based in part upon capabilities of particular three dimensional printing equipment.

If certain graphic properties are deemed unprintable, in some implementations, the model is modified to include only printable features (106). In some implementations, the three dimensional model or graphic representation thereof is automatically adjusted to remove features identified as being unprintable. In other implementations, the user may be prompted to adjust one or more settings to remove unprintable features. For example, turning to FIG. 3A, a dialogue box 302 alerts the user as to an unprintable feature of dashed lines. The user is provided the opportunity for automatic adjustment via selection of a remove all control 304a. Alternatively, the user may select an "open" control 304b to open a model properties dialog box for manual adjustment of the graphic properties associated with the three dimensional molecular model (illustrated here as a ball-and-stick model). The user may instead chose to cancel the print command through selection of a cancel control 304c. In this manner, for example, the user may select a different model style for printing, such as a cylindrical bonds model. Various styles of graphic representation of a three dimensional molecular model, for example, are illustrated in a representation menu 202 of FIG. 2A.

Figure 3B:
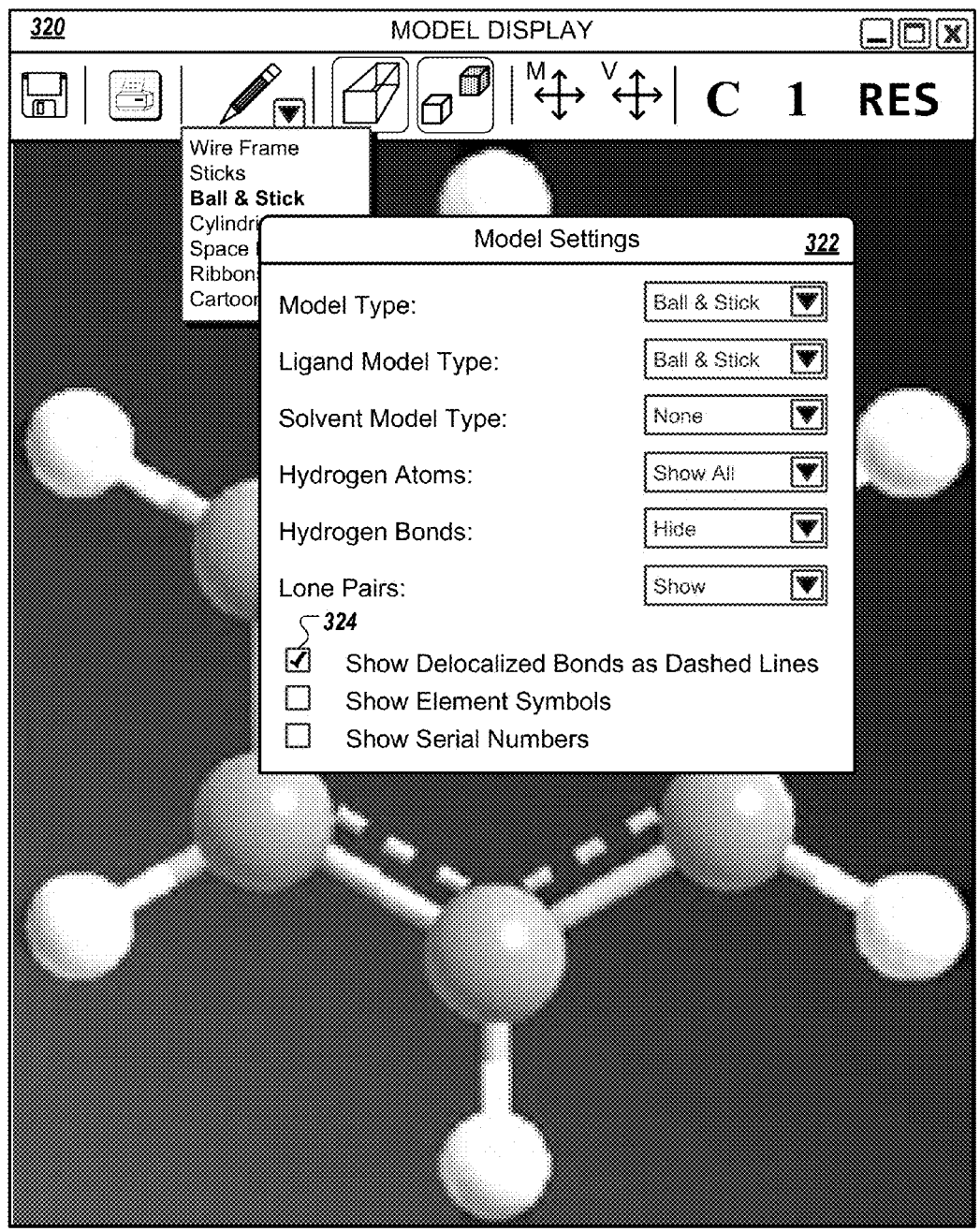
Figure 3C:
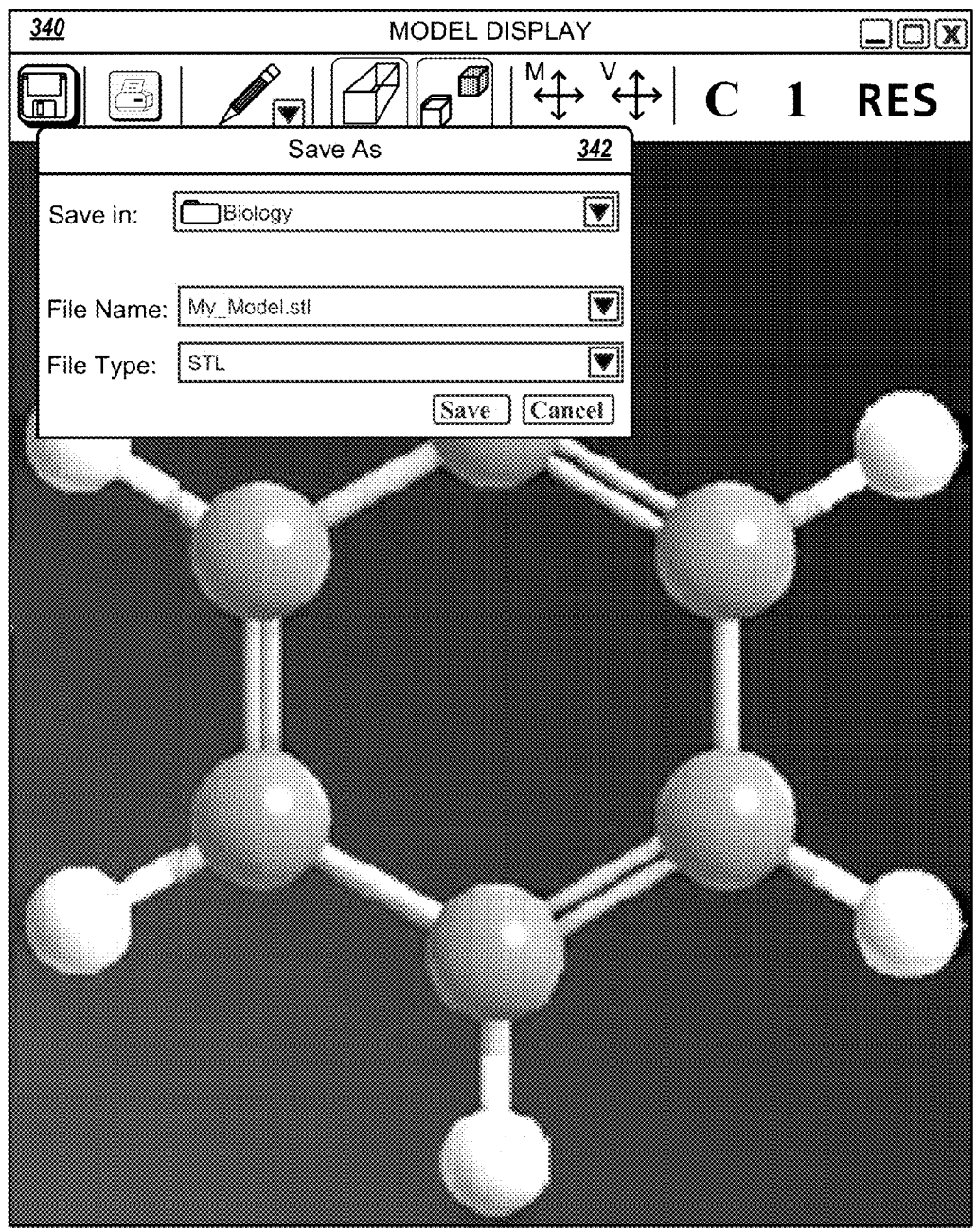

If the user chooses the "open" control 304b, in some implementations, the user is presented with a model settings dialogue box 322, illustrated in FIG. 3B. As illustrated, a checkbox 324 is selected, setting "show delocalized bonds as dashed lines". By deselecting the checkbox 324, for example, the user may overcome the print error.

Returning to method 100 of FIG. 1, in some implementations, the model is reviewed to identify that the three dimensional model (or graphic representation thereof) defines a self-supporting structure (108). Certain three dimensional printing equipment requires that a structure identified for printing has a substantially self-supporting structure such that the structure will not collapse upon printing. For example, for particular three dimensional printing equipment, the ball-and-stick model illustrated in a screen shot 340 of FIG. 3C may be considered unprintable due lacking a self-supporting structure.

In some implementations, the user is prompted regarding incompatibility of the three dimensional model (or graphic representation thereof) with the available three dimensional printing equipment (110). For example, the user may be offered the opportunity to select a cartoon model or space filling model (e.g., as illustrated in the screen shot 200 of FIG. 2A) rather than the present ball-and-stick model.

Returning to 108, in some implementations, although the model defines a self-supporting structure, the model may additionally contain a portion which is not self-supporting (112). Depending upon the type of model, a portion of the model representing a self-supporting structure may be printed, while the remainder of the model may be identified as unprintable. For example, particular three dimensional printing equipment may be capable of printing the ribbon protein model illustrated in the screen shot 250 of FIG. 2B after removal of the ribbon portion. In some implementations, the user is prompted for authorization to convert to a representation having printable features (114). For example, the user may be prompted to authorize removal of the ribbon portion of the ribbon protein model illustrated in the screen shot 250 of FIG. 2B prior to continuing. Alternatively, the user may opt to convert to a different graphic representation of the model, such as a cartoon representation.

In some implementations, the surfaces of the three dimensional model (or graphic representation thereof) are converted to a polygon mesh representation (116). A polygon mesh includes a collection of vertices, edges, and faces used to define the surface region of a three-dimensional polyhedral object. The faces may be formed of simple convex polygons, such as triangles or quadrilaterals.

In some implementations, in preparation for conversion to a polygon mesh, the three dimensional model (or graphic representation thereof) is simplified for conversion purposes. For example, inner spaces of the three dimensional model may be closed or removed to reduce the complexity of creating a surface mesh. In another example, a complexity of the topography of a detailed portion of the three dimensional model may be reduced. For example, a particular texture applied to a region of the three dimensional model may be simplified or removed.

During conversion to the polygon mesh representation, in some implementations, smoothing groups may be identified to determine smooth shading surfaces for the model. For example, turning to the space filling model illustrated in FIG. 2A, each rounded space filling atom may be grouped within a particular smoothing group such that the partial spheres are treated as a single surface for smoothing purposes. The surface of the three dimensional model, in some implementations, is approximated using one or more iso-contouring techniques, such as a marching cube method algorithm (e.g., as described in William E. Lorensen, Harvey E. Cline: *Marching Cubes: A high resolution 3D surface construction algorithm*. In: *Computer Graphics*, Vol. 21, Nr. 4, July 1987). In certain embodiments, a further step includes removing any portions of the model that are internal, or encapsulated by other portions of the model. For example, a portion of a 3D surface model that is internal, enclosed by, or encapsulated by the rest of the model would not be visible, may not be printable, and should be removed from the model.

In some implementations, the vertices of the polygon mesh representation include property information, such as color, texture, and/or hardness. For example, based upon a type of structural element (e.g., atom, bond, protein, etc.) and/or graphic properties associated with particular structural elements portrayed within the graphic representation of the molecular model, properties of the three dimensional model may be migrated to identify printing properties of the polygon mesh representation.

In some implementations, the polygon mesh representation is validated (118). For example, the polygon mesh representation may be analyzed to identify any inner vertices and/or mesh openings that fail to represent a single, "watertight" wrapped surface of the polygon mesh representation of the three dimensional molecular structure.

If any inner vertices and/or mesh openings are discovered (120), in some implementations, the identified defects are corrected within the polygon mesh representation (122). For example, a region including a hole may be re-triangulated to patch the opening within the surface. Inner vertices, in another example, may be deleted from the polygon mesh representation. Thus, portions of the model that are internal, or encapsulated by other portions of the model would be removed.

In some implementations, if the command entered by the user was a print command (124), computer aided design-formatted instructions are issued to an identified three dimensional printing equipment (126). A polygon mesh defined using the standardized STL format, for example, may be provided to three dimensional printing equipment in communication with the computing device performing the method 100.

In some implementations, if the command entered by the user was a save command (124), the polygon mesh representation is saved as a computer aided design-formatted file (128). For example, the polygon mesh representation may be saved in STL format.

Figure 4:
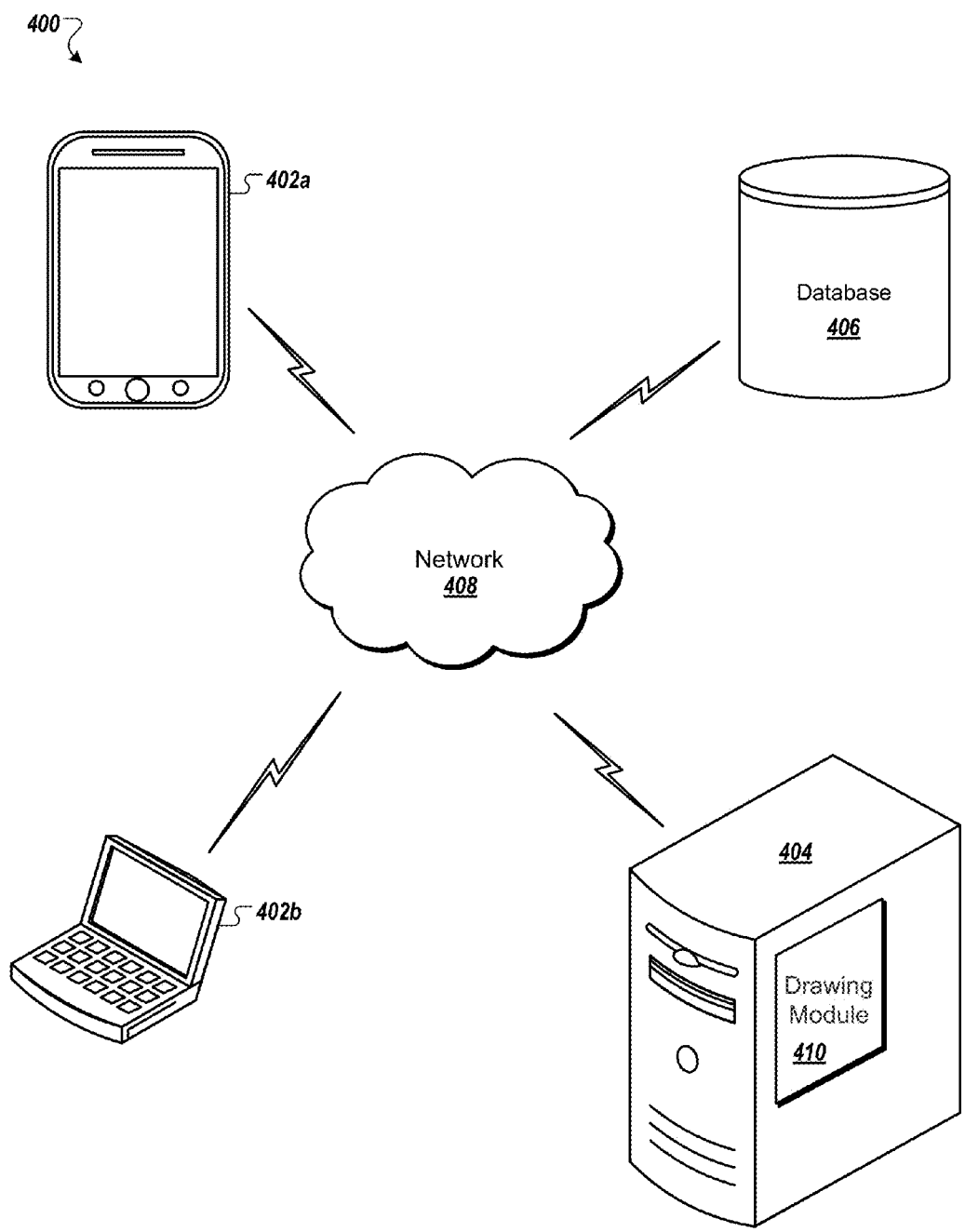
FIG. 4 is a schematic diagram of an example system for converting three dimensional graphic representations of molecular structures to computer aided design format.

FIG. 4 depicts an example system 400 for converting three dimensional graphic representations of molecular structures to computer aided design format. The system 400 includes client nodes 402a and 402b, a server node 404, a database 406, and, for enabling communications therebetween, a network 408. As illustrated, the server node 404 may include a drawing module 410.

The network 408 may be, for example, a local-area network (LAN), such as a company or laboratory Intranet, a metropolitan area network (MAN), or a wide area network (WAN), such as the Internet. Each of the client nodes 402, server node 404, and the database 406 may be connected to the network 408 through a variety of connections including, but not limited to, standard telephone lines, LAN or WAN links (e.g., T1, T3, 56 kb, X.25), broadband connections (e.g., ISDN, Frame Relay, ATM), or wireless connections. The connections, moreover, may be established using a variety of communication protocols (e.g., HTTP, TCP/IP, IPX, SPX, NetBIOS, NetBEUI, SMB, Ethernet, ARCNET, Fiber Distributed Data Interface (FDDI), RS232, IEEE 802.11, IEEE 802.11a, IEEE 802.11b, IEEE 802.11g, and direct asynchronous connections).

The client node 402a may be any type of wireless device, information appliance, tablet computer, personal digital assistant, cellular phone, handheld device, or other portable computing device that is capable of both presenting information/data to, and receiving commands from, a user of the client node 402a (e.g., an analytical chemist). Similarly, the client node 402b may be any type of personal computer, Windows-based terminal, network computer, wireless device, information appliance, RISC Power PC, X-device, workstation, mini computer, main frame computer, set top box, or other computing device that is capable of both presenting information/data to, and receiving commands from, a user of the client node 402b. The client nodes 402 may include, for example, a graphical display device (e.g., a touch screen or a computer monitor), a data entry device (e.g., a keyboard, a touch screen, or a mouse pad), persistent and/or volatile storage (e.g., computer memory), and a processor. In one embodiment, the client node 402 includes a web browser, such as, for example, Internet Explorer® developed by Microsoft Corporation of Redmond, Wash., to connect to the World Wide Web.

For its part, the server node 404 may be any computing device that is capable of receiving information/data from and delivering information/data to the client nodes 402, for example over the network 408, and that is capable of querying, receiving information/data from, and delivering information/data to the server node 404. For example, as further explained below, the server node 404 may receive input (e.g., a multi-touch gesture) from a user of the client node 402, create or edit a chemical structure representation according to the input, and present or display the chemical structure representation to the user at the client node 402. The server node 404 may include a processor and persistent and/or volatile storage, such as computer memory.

The server node 404 may be any computing device that is capable of storing and managing collections of data, such as data relating to chemical structure representations. The chemical structure representations may be, for example, of the type described in related U.S. Pat. No. 8,433,723, filed May 3, 2011, titled "Systems, Methods, and Apparatus for Processing Documents to Identify Structures," and related U.S. application Ser. No. 13/239,069, filed, Sep. 21, 2011, titled "Systems, Methods, and Apparatus for Facilitating Chemical Analyses," and related International Patent Application No. PCT/US12/26574, filed Feb. 24, 2012, titled "Systems, Methods, and Apparatus for Drawing Chemical Structures Using Touch and Gestures," the disclosures of each of which are hereby incorporated by reference herein in their entireties.

As used herein, the term "server node" is broadly used to refer to any repository of information. The data stored within the server node 404 may be harvested from the server node 404 in any manner. In one embodiment, the harvesting is performed utilizing indexing and structure recognition algorithms, and the harvested data is connected together by examining and correlating the disjointed information that is found.

The drawing module 410 of the server node 404 may be implemented as any software program and/or hardware device, for example an application specific integrated circuit (ASIC) or a field programmable gate array (FPGA), that is capable of providing the functionality described herein. It will be understood by one having ordinary skill in the art, however, that the illustrated module 410, and the organization of the server node 404, are conceptual, rather than explicit, requirements. For example, it should be understood that the drawing module 410 may in fact be implemented as multiple modules, such that the functions performed by the single module, as described herein, are in fact performed by the multiple modules.

Although not shown in FIG. 4, any or all of the client nodes 402, the server node 404, and the database 406 may also include its own transceiver (or separate receiver and transmitter) that is capable of receiving and transmitting communications, including requests, responses, and commands, such as, for example, inter-processor communications and networked communications. The transceivers (or separate receivers and transmitters) may each be implemented as a hardware device, or as a software module with a hardware interface.

It will also be understood by those skilled in the art that FIG. 4 is a simplified illustration of the system 400 and that it is depicted as such to facilitate the explanation of various embodiments of the present disclosure. Moreover, the system 400 may be modified in a variety of manners without departing from the spirit and scope of the present disclosure. For example, rather than being implemented on a single server node 404, the drawing module 410 may instead be implemented on a different computing device (not shown) and such computing devices may communicate with one another directly, over the network 408, or over another additional network (not shown). In yet another example, the functionality of the server node 404 may in fact be resident on the server node 404 (e.g., be implemented in the computer memory thereof). Additional options are for the server node 404 and/or the database 406 to be local to the client node 402 (such that they may all communicate directly without using the network 408), or for the functionality of the server node 404 and/or the database 406 to be implemented on the client node 402 (e.g., for the drawing module 410 and/or the server node 404 to reside on the client node 402). As such, the depiction of the system 400 in FIG. 4 is non-limiting.

In certain embodiments, the system 400 allows a user to view, create, and/or edit three dimensional models of molecular structures. The system 400, in some embodiments, allows a user to draw and edit a graphic representation of a molecular structure using a mouse, stylus, keypad, trackball, or other input interface, such as an input interface at a client personal computer 402b. The input interface, in some implementations, may include a natural language processing module capable of converting utterances to a series of commands for activating controls of the user interface.

In general, the drawing module 410 in the server node 404 is configured to draw or revise a three dimensional graphic representation of a molecular structure according to the input from the user, as explained above with respect to the prior figures. The drawing module 410 may then provide an image (e.g., a collection of pixels) of the graphic representation of the three dimensional molecular structure for presentation to the user on the graphical display of the particular client node 402. Additionally, the drawing module 410 may automatically adjust (e.g., remove unprintable features) a three dimensional graphic representation of a molecular structure for printing purposes. In general, the system 400 may be used to perform any of the methods described herein.

Figure 5:
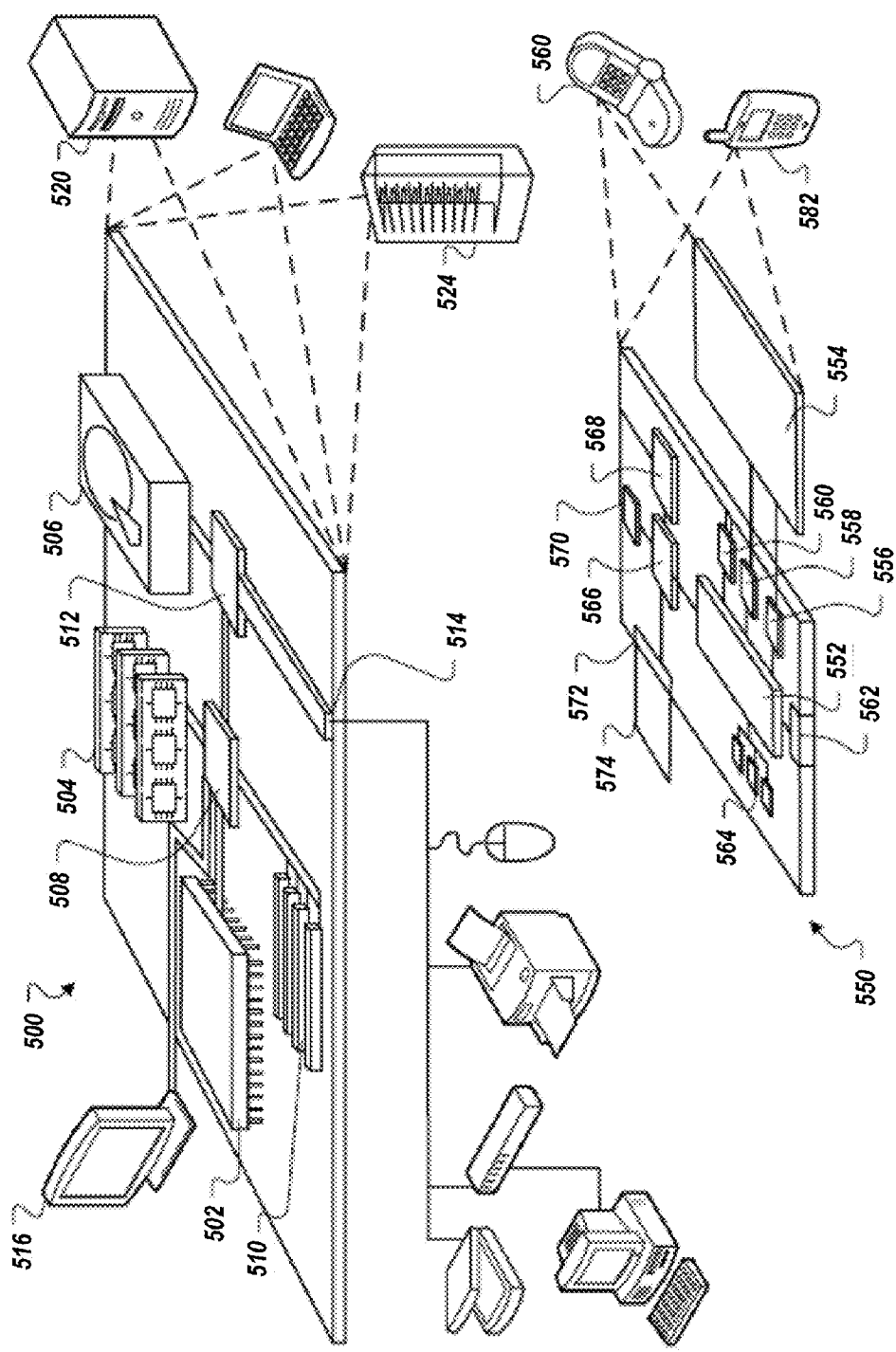
FIG. 5 is a block diagram of an example computing device and an example mobile computing device.

FIG. 5 shows an example of a computing device 500 and a mobile computing device 550 that can be used to implement the techniques described in this disclosure. The computing device 500 is intended to represent various forms of digital computers, such as laptops, desktops, workstations, personal digital assistants, servers, blade servers, mainframes, and other appropriate computers. The mobile computing device 550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 500 includes a processor 502, a memory 504, a storage device 506, a high-speed interface 508 connecting to the memory 504 and multiple high-speed expansion ports 510, and a low-speed interface 512 connecting to a low-speed expansion port 514 and the storage device 506. Each of the processor 502, the memory 504, the storage device 506, the high-speed interface 508, the high-speed expansion ports 510, and the low-speed interface 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as a display 516 coupled to the high-speed interface 508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 504 stores information within the computing device 500. In some implementations, the memory 504 is a volatile memory unit or units. In some implementations, the memory 504 is a non-volatile memory unit or units. The memory 504 may also be another form of computer-readable medium, such as a magnetic or optical disk.

The storage device 506 is capable of providing mass storage for the computing device 500. In some implementations, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 502), perform one or more methods, such as those described above. The instructions can also be stored by one or more storage devices such as computer- or machine-readable mediums (for example, the memory 504, the storage device 506, or memory on the processor 502).

The high-speed interface 508 manages bandwidth-intensive operations for the computing device 500, while the low-speed interface 512 manages lower bandwidth-intensive operations. Such allocation of functions is an example only. In some implementations, the high-speed interface 508 is coupled to the memory 504, the display 516 (e.g., through a graphics processor or accelerator), and to the high-speed expansion ports 510, which may accept various expansion cards (not shown). In the implementation, the low-speed interface 512 is coupled to the storage device 506 and the low-speed expansion port 514. The low-speed expansion port 514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. In addition, it may be implemented in a personal computer such as a laptop computer 522. It may also be implemented as part of a rack server system 524. Alternatively, components from the computing device 500 may be combined with other components in a mobile device (not shown), such as a mobile computing device 550. Each of such devices may contain one or more of the computing device 500 and the mobile computing device 550, and an entire system may be made up of multiple computing devices communicating with each other.

The mobile computing device 550 includes a processor 552, a memory 564, an input/output device such as a display 554, a communication interface 566, and a transceiver 568, among other components. The mobile computing device 550 may also be provided with a storage device, such as a micro-drive or other device, to provide additional storage. Each of the processor 552, the memory 564, the display 554, the communication interface 566, and the transceiver 568, are interconnected using various buses, and several of the components may be mounted on a common motherboard or in other manners as appropriate.

The processor 552 can execute instructions within the mobile computing device 550, including instructions stored in the memory 564. The processor 552 may be implemented as a chipset of chips that include separate and multiple analog and digital processors. The processor 552 may provide, for example, for coordination of the other components of the mobile computing device 550, such as control of user interfaces, applications run by the mobile computing device 550, and wireless communication by the mobile computing device 550.

The processor 552 may communicate with a user through a control interface 558 and a display interface 556 coupled to the display 554. The display 554 may be, for example, a TFT (Thin-Film-Transistor Liquid Crystal Display) display or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may provide communication with the processor 552, so as to enable near area communication of the mobile computing device 550 with other devices. The external interface 562 may provide, for example, for wired communication in some implementations, or for wireless communication in other implementations, and multiple interfaces may also be used.

The memory 564 stores information within the mobile computing device 550. The memory 564 can be implemented as one or more of a computer-readable medium or media, a volatile memory unit or units, or a non-volatile memory unit or units. An expansion memory 574 may also be provided and connected to the mobile computing device 550 through an expansion interface 572, which may include, for example, a SIMM (Single In Line Memory Module) card interface. The expansion memory 574 may provide extra storage space for the mobile computing device 550, or may also store applications or other information for the mobile computing device 550. Specifically, the expansion memory 574 may include instructions to carry out or supplement the processes described above, and may include secure information also. Thus, for example, the expansion memory 574 may be provide as a security module for the mobile computing device 550, and may be programmed with instructions that permit secure use of the mobile computing device 550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 552), perform one or more methods, such as those described above. The instructions can also be stored by one or more storage devices, such as one or more computer- or machine-readable mediums (for example, the memory 564, the expansion memory 574, or memory on the processor 552). In some implementations, the instructions can be received in a propagated signal, for example, over the transceiver 568 or the external interface 562.

The mobile computing device 550 may communicate wirelessly through the communication interface 566, which may include digital signal processing circuitry where necessary. The communication interface 566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 568 using a radio-frequency. In addition, short-range communication may occur, such as using a Bluetooth®, Wi-Fi™, or other such transceiver (not shown). In addition, a GPS (Global Positioning System) receiver module 570 may provide additional navigation- and location-related wireless data to the mobile computing device 550, which may be used as appropriate by applications running on the mobile computing device 550.

The mobile computing device 550 may also communicate audibly using an audio codec 560, which may receive spoken information from a user and convert it to usable digital information. The audio codec 560 may likewise generate audible sound for a user, such as through a speaker, e.g., in a handset of the mobile computing device 550. Such sound may include sound from voice telephone calls, may include recorded sound (e.g., voice messages, music files, etc.) and may also include sound generated by applications operating on the mobile computing device 550.

The mobile computing device 550 may be implemented in a number of different forms, as shown in the figure. For example, it may be implemented as a cellular telephone 580. It may also be implemented as part of a smart-phone 582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

It should also be noted that embodiments of the present disclosure may be provided as one or more computer-readable programs embodied on or in one or more articles of manufacture. The article of manufacture may be any suitable hardware apparatus, such as, for example, a floppy disk, a hard disk, a CD ROM, a CD-RW, a CD-R, a DVD ROM, a DVD-RW, a DVD-R, a flash memory card, a PROM, a RAM, a ROM, or a magnetic tape. In general, the computer-readable programs may be implemented in any programming language. Some examples of languages that may be used include C, C++, or Java. The software programs may be further translated into machine language or virtual machine instructions and stored in a program file in that form. The program file may then be stored on or in one or more of the articles of manufacture.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

In view of the structure, functions and apparatus of the systems and methods described here, in some implementations, systems and methods for converting three dimensional graphic representations of molecular structures to computer aided design format for three dimensional printing purposes are provided. Having described certain implementations of methods and apparatus for converting three dimensional graphic representations of molecular structures to computer aided design format for printing purposes, it will now become apparent to one of skill in the art that other implementations incorporating the concepts of the disclosure may be used. Therefore, the disclosure should not be limited to certain implementations, but rather should be limited only by the spirit and scope of the following claims.

What is claimed is:

1. A system for converting graphic representations of three dimensional molecular models into computer-aided design format, the system comprising:
   a processor; and
   a memory having a set of instructions stored thereon, wherein the instructions, when executed, cause the processor to:
      receive, within a chemical structure rendering application, a request identifying a three dimensional model of a chemical and/or biological structure wherein the request is one of a file save request and a print request,
      associate the request with conversion to a computer-aided design format,
      access the three dimensional model,
      identify a surface region of a graphic representation of the three dimensional model,
      convert the surface region into a polygon mesh representation, and
      validate the polygon mesh representation, wherein validating the polygon mesh representation comprises analyzing the polygon mesh representation to identify any inner vertices and/or mesh openings that fail to represent a single watertight wrapped surface of the polygon mesh representation of the three dimensional model.

2. The system of claim 1, wherein the instructions cause the processor to, after converting the surface region into the polygon mesh representation:
   remove one or more of the inner vertices identified by the processor.

3. The system of claim 1, wherein the instructions cause the processor to adjust the polygon mesh representation to close one or more openings.

4. The system of claim 1, wherein the instructions cause the processor to identify one or more unprintable features of the graphic representation.

5. The system of claim 4, wherein the instructions cause the processor to identify a type of three dimensional printing equipment, wherein identifying the one or more unprintable features comprises identifying, based upon printer capabilities associated with the type of the three dimensional printing equipment, at least one of the one or more unprintable features.

6. The system of claim 4, wherein the instructions cause the processor to, after identifying the one or more unprintable features, cause presentation of a prompt within a user interface of the application, prompting modification of one or more feature settings of the three dimensional model to convert the graphic representation to a printable graphic representation having printable features.

7. The system of claim 6, wherein the instructions cause the processor to:
receive an acknowledgement of authorization; and
automatically adjust the one or more feature settings.

8. The system of claim 1, wherein the instructions cause the processor to verify the graphic representation comprises a self-supporting structure.

9. The system of claim 1, wherein the polygon mesh representation comprises a triangular mesh.

10. The system of claim 1, wherein the instructions cause the processor to, after converting the surface region into the polygon mesh representation, save the polygon mesh representation as a computer aided design file.

11. The system of claim 10, wherein the computer aided design file is in STL file format.

12. The system of claim 1, wherein the instructions cause the processor to, after converting the surface region into the polygon mesh representation, issue print instructions comprising the polygon mesh representation to a three dimensional printing equipment.

13. The system of claim 12, wherein the three dimensional printing equipment is one of rapid prototyping equipment, additive manufacturing equipment, and a three dimensional printer.

14. The system of claim 1, wherein the three dimensional model is one of a ribbon protein model, a space filling model, a cartoon model, and a ball and stick model.

15. The system of claim 1, wherein the chemical structure rendering application is one of an electronic notebook application and a chemistry modeling application.

16. The system of claim 1, wherein the three dimensional model comprises one or more of an XML file and a PDB file.

17. The system of claim 1, wherein the three dimensional model comprises a .c3xml file.

18. A method comprising:
receiving, by a processor of a computing device, within a chemical structure rendering application, a request identifying a three dimensional model of a chemical and/or biological structure, wherein the request is one of a file save request and a print request;
associating, by the processor, the request with conversion to a computer-aided design format;
accessing, by the processor, the three dimensional model;
identifying, by the processor, a surface region of a graphic representation of the three dimensional model;
converting, by the processor, the surface region into a polygon mesh representation; and
validating, by the processor, the polygon mesh representation, wherein validating the polygon mesh representation comprises analyzing the polygon mesh representation to identify any inner vertices and/or mesh openings that fail to represent a single watertight wrapped surface of the polygon mesh representation of the three dimensional model.

19. The method of claim 18, further comprising printing, by a three dimensional printer, the three dimensional model using the polygon mesh representation.

20. A non-transitory computer readable medium having instructions stored thereon, wherein the instructions, when executed by a processor, cause the processor to:
receive, within a chemical structure rendering application, a request identifying a three dimensional model of a chemical and/or biological structure, wherein the request is one of a file save request and a print request;
associate the request with conversion to a computer-aided design format;
access the three dimensional model;
identify a surface region of a graphic representation of the three dimensional model;
convert the surface region into a polygon mesh representation; and
validate the polygon mesh representation, wherein validating the polygon mesh representation comprises analyzing the polygon mesh representation to identify any inner vertices and/or mesh openings that fail to represent a single watertight wrapped surface of the polygon mesh representation of the three dimensional model.

21. The computer readable medium of claim 20, wherein the instructions, when executed by the processor, cause the processor to print, by a three dimensional printer, the three dimensional model using the polygon mesh representation.

22. A system for converting graphic representations of three dimensional molecular models into computer-aided design format, the system comprising:
a processor; and
a memory having a set of instructions stored thereon, wherein the instructions, when executed, cause the processor to:
receive, within a chemical structure rendering application, a request identifying a three dimensional model of a chemical and/or biological structure, wherein the request is one of a file save request and a print request,
associate the request with conversion to a computer-aided design format,
access the three dimensional model,
identify a surface region of a graphic representation of the three dimensional model,
convert the surface region into a polygon mesh representation,
identify one or more unprintable features of the graphic representation, and
cause presentation of a prompt within a user interface of the application, prompting modification of one or more feature settings of the three dimensional model to convert the graphic representation to a printable graphic representation having printable features.

* * * * *